United States Patent [19]

Le Floc'h et al.

[11] Patent Number: 5,195,116
[45] Date of Patent: Mar. 16, 1993

[54] COMPTON-EFFECT METHOD AND SYSTEM FOR LOCATING A PLANE SEPARATING TWO MEDIA OF DIFFERENT DENSITIES

[75] Inventors: Christian M. Le Floc'h, Blanquefort; Pierre Sarrazin, Bordeaux; Daniel M. Babot; Gilles G. Peix, both of Villeurbanne, all of France

[73] Assignee: Societe Anonyme dite: Aerospatiale Societe Nationale Industrielle, Paris, France

[21] Appl. No.: 823,818

[22] Filed: Jan. 22, 1992

[30] Foreign Application Priority Data

Jan. 30, 1991 [FR] France ................... 91 01051

[51] Int. Cl.$^5$ .............................................. G01B 15/02
[52] U.S. Cl. ......................................... 378/89; 378/86
[58] Field of Search ................................ 378/89, 86

[56] References Cited

U.S. PATENT DOCUMENTS 4,165,460 8/1979 Rose et al. ...................... 378/89

FOREIGN PATENT DOCUMENTS 0380226 8/1990 European Pat. Off. .

OTHER PUBLICATIONS

Patent Abstracts of Japan, vol. 7, No. 48, (P-178)(11983) Feb. 24, 1983.

*Primary Examiner*—Craig E. Church
*Attorney, Agent, or Firm*—Marshall, O'Toole, Gerstein, Murray & Bicknell

[57] ABSTRACT

A method and a system for enabling high accuracy measurements to be obtained of the location of a plane separating two media of different densities by using the Compton effect, and application thereof to measuring the thicknesses of layers. A measurement assembly constituted by a transmitter and a receiver of X-rays or gamma rays which are focused in emission and in reception irradiates an elementary volume of said media, and is displaced perpendicularly to the plane between said media, and a fifth signal is calculated representative of the extent by which the derivative of the detected signal relative to the displacement exceeds a threshold, after which the barycenter of displacements corresponding to the most recent sequence of said same-sign fifth signals is calculated, with the displacements being weighted by the corresponding one of said fifth signals.

6 Claims, 2 Drawing Sheets

COMPTON-EFFECT METHOD AND SYSTEM FOR LOCATING A PLANE SEPARATING TWO MEDIA OF DIFFERENT DENSITIES

The present invention relates to a method and to a system enabling high-accuracy measurements to be made of the location of a plane separating two media of different densities by using the Compton effect, and it also relates to the application thereof to measuring layer thicknesses.

BACKGROUND OF THE INVENTION

Proposals have already been made to use the Compton effect to determine the position of a separation plane between two media of different densities. Thus, in an article entitled "Compton backscatter tomography of low atomic number materials with the ComScan system", published in January 1989 by J. Kosanetzky, G. Harding, K. H. Fisher, and A. Meyer, of Philips Forschungslaboratorium Hamburg, the principle of using the Compton effect has already been described, together with a device for performing tomography on a body by subjecting it to X-rays or to gamma rays, which rays produce omnidirectional radiation representative of the density of the irradiated volume of said body by interacting with the electrons in the atoms of the body. An emitter of radiation produces a relatively fine pencil that passes through the body under investigation, and the Compton effect radiation therefrom is detected by receivers. A mechanism enables the apparatus to be displaced as a whole perpendicularly to the surface of the body through which the radiation penetrates, thereby taking measurements at various depths beneath said surface.

However, such a apparatus suffers from the drawback of using a plurality of emitters of radiation and a plurality of associated pairs of detectors. The detectors are also large in area with only a small portion thereof being in use at any given instant, such that their unused portions give rise to background noise in the electronic detection system and, in addition, receive Compton effect emissions that have been subjected to scatters on a plurality of occasions in volumes of the body that are not directly irradiated. Taken together, these interfering phenomena limit the accuracy of measurement.

The present invention seeks to obviate these drawbacks by providing a method and apparatus that improve the spatial resolution of measurements enabling the plane between two media of different densities to be located.

SUMMARY OF THE INVENTION

To this end, the present invention provides a system for locating the separation plane between two media of different densities, relative to a reference plane parallel to said separation plane and at a fixed distance therefrom, said media being suitable for being irradiated by a beam of X-rays or of gamma rays from an emitter, and producing scattering by the Compton effect, which scattering is detected by a receiver that responds thereto by providing a first signal, said receiver being carried by a support; the system being remarkable in that:

said emitter emits at regulated intensity; and
said system further includes:
a time base emitting sequencing commands for cycles in a sequence of displacement, measurement, and calculation operations, with one such sequence of cycles corresponding to measurements relating to a sequence of analyzed volumes disposed along a line substantially perpendicular to said reference plane;

displacement apparatus for controlled relative displacement of said support relative to said reference plane and substantially perpendicular thereto, said apparatus being controlled by the time base;

a first collimator including at least one slot, said collimator being fixed on said support and providing an elementary beam passing through said slot and directed towards an elementary volume of elongate shape extending parallel to the looked-for separation plane between the media, which elementary volume is capable of being occupied by said media, said collimator being situated at the outlet from the emitter;

a second collimator including a plurality of slots, said second collimator being fixed on said support, its slots converging on said elementary volume such that the elementary beams passing through the slots are concentrated in said elementary volume, which second collimator is situated in front of the detector of the receiver;

said support, said emitter, said first and second collimators, and said receiver constituting a measurement assembly whose position relative to said reference plane is identical to that of said support;

an integrator for integrating relative to time and under the control of said time base, said integrator receiving said first signal and providing a second signal representative of the time integral of said first signal over a time period defined by the time base;

a subtractor controlled by said time base, receiving said second signal and responding thereto by providing a third signal representative of the difference between said second signal relating to the current cycle and the second signal relating to the preceding cycle;

first calculation means controlled by said time base, receiving said third signal and responding thereto by providing a fourth signal representative of the derivative of said third signal relative to the relative displacement distance between the measurement assembly and the reference plane;

second calculation means controlled by said time base, receiving said fourth signal and responding thereto by providing a fifth signal representative of a number having the same sign as the fourth signal and whose absolute value is equal either:
  to the difference obtained by subtracting a predetermined positive number from said fourth signal, so long as the result is positive; or else
  to zero whenever said result is negative or zero.

third calculation means controlled by said time base, having a first input receiving said fifth signal and having a second input receiving the command issued by the time base for causing relative displacement of said support relative to the reference plane in a direction substantially perpendicular thereto, said third calculation means storing said fifth signal and, whenever said fifth signal is zero or opposite in sign to the fifth signal generated during the preceding cycle, providing a sixth signal representative of a displacement distance of the measurement assembly relative to its initial position at the beginning of said sequence of cycles, which distance corresponds to the relative position of the barycentre of successive distances relating to the most recent sequence of non-zero and same-sign fifth signals calculated during the preceding cycles, with the value of each such fifth signal of such a sequence weighting the displacement distance at which the measurement assembly is to be found from its initial position during the cycle in which said fifth signal is generated, said barycentre being situated in a separation plane between two adjacent media.

It will be observed that because of the plurality of slots in said second collimator, a maximum number of photons backscattered by said elementary volume are collected, such that the count time can be divided by the number of slots in said second collimator.

Further, the measurements of received radiation are integrated and therefore contain less noise, thereby providing better accuracy for calculations performed on the basis of said measurements. Such calculations include calculating a barycentre, taking account of the most recent measurements performed pro rata their magnitude, thus making it possible to situate the separation plane between adjacent media accurately.

Preferably, said first collimator includes a plurality of slots, and the elementary beams passing through said slots converge on said elementary volume.

In addition, the system is remarkable in that it includes apparatus for displacing the measurement assembly relative to the media in a direction parallel to said reference plane. It is thus possible to run sequences of measurement cycles automatically one after another.

Further, since the system of the invention includes a collimator having a plurality of slots, it is remarkable in that all of the elementary beams (where i=1, 2, 3, etc. . . . ), each transmitted via one of the slots are concentrated in the same common volume, one of whose dimensions lies in the range 0.1 mm to 0.4 mm.

As a result, the elementary volume defined by the intersection of two such volumes has two dimensions lying in the range 0.1 mm to 0.4 mm, thereby improving measurement accuracy.

The invention also provides a method of localizing the separation plane between two media of different densities, relative to a reference plane parallel to said separation plane and at a fixed distance therefrom, said media being suitable for being irradiated by a beam of X-rays or of gamma rays from an emitter and producing Compton effect scattering that is detected by a receiver which responds thereto by providing a first signal, said receiver being carried by a support, the method being remarkable in that it comprises a sequence of cycles corresponding to measurements relating to a sequence of analyzed volumes spaced apart along a line substantially perpendicular to said reference plane, each of said cycles including the following steps:

controlling a displacement apparatus to obtain controlled displacement of said support relative to said reference plane in a direction substantially perpendicular thereto;

emitting a beam of X-rays or of gamma rays at regulated intensity from an emitter fixed on said support;

spatially filtering said beam by passing it through a first collimator that includes at least one slot, the collimator being fixed on said support and the elementary beam passing through said slot being directed towards an elementary volume of elongate shape extending parallel to the looked-for separation plane between the media, which elementary volume is capable of being occupied by said media, said first collimator being situated at the outlet from the emitter;

spatially filtering the Compton effect radiation emitted by said elementary volume by passing the radiation through a second collimator that includes a plurality of slots, the second collimator being fixed on said support, the slots converging on said elementary volume such that the elementary beams passing through the slots are concentrated in said elementary volume, the collimator being situated in front of the detector of the receiver, said support, said emitter, said first and second collimators and said receiver constituting a measurement assembly whose position relative to the said reference plane is identical to that of said support;

integrating said first signal relative to time in an integrator for performing integration relative to time under the control of the time base, which integrator receives said first signal and provides a second signal representative of the time integral of said first signal over a time period defined by the time base;

subtracting the second signal relating to the preceding cycle from said second signal relating to the current cycle in a subtractor controlled by said time base and receiving said second signal, thereby obtaining a third signal;

differentiating said third signal relative to the relative displacement distance between the measurement assembly and the reference plane in a first calculation means controlled by said time base and receiving said third signal, thereby obtaining a fourth signal;

calculating a number in a second calculation means controlled by said time base and receiving said fourth signal, the sign of said number being identical to that of the fourth signal, and its absolute value being equal either to the difference obtained by subtracting a predetermined positive number from said fourth signal, when the result of the subtraction is positive, or else is equal to zero when said result is negative or zero, thereby obtaining a fifth signal;

calculating a sixth signal in a third calculation means controlled by said time base and having a first input receiving said fifth signal and a second input receiving the command issued by the time base to cause relative displacement of said support relative to the reference plane and substantially perpendicular thereto, the third calculation means storing said fifth signal and generating said sixth signal when said fifth signal is zero or of opposite sign to the fifth signal generated during the preceding cycle, said sixth signal being representative of a displacement distance of the measurement assembly relative to its initial position at the beginning of said sequence of cycles, which distance corresponds to the relative position of the barycentre of successive distances relating to the most recent sequence of non-zero fifth signals of the same sign calculated during the preceding cycles, the value of each such fifth signal of such a sequence weighting the displacement distance at which the measurement assembly is to be found from its initial position during the cycle in which said fifth signal is generated, said barycentre being situated in a separation plane between two adjacent media.

As a result, calculating the position of the plane separating adjacent media takes account of a plurality of successive measurements, thereby making it possible to achieve greater accuracy.

Advantageously, a first collimator is used that is provided with a plurality of slots passed through by a plurality of elementary beams converging on said elementary volume.

BRIEF DESCRIPTION OF THE DRAWINGS

An embodiment of the invention is described by way of example with reference to the accompanying drawings, in which.

DETAILED DESCRIPTION

Figure 1:
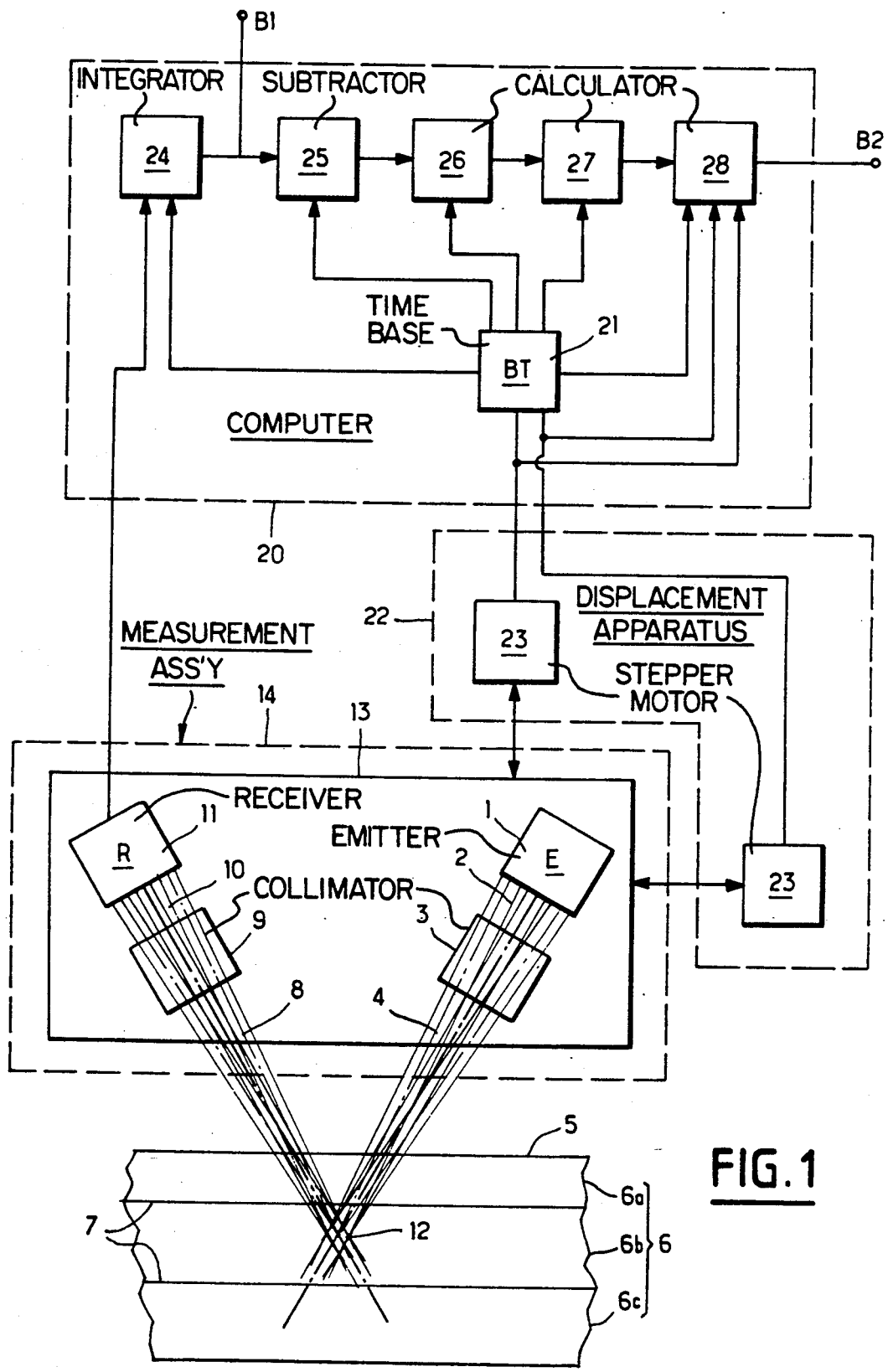
FIG. 1 is a block diagram of a system for determining the position of a plane separating two media of different densities, with the position being determined on the basis of measurements that use the Compton effect.

In FIG. 1, an emitter E referenced 1 is constituted by a stabilized and screened source that emits a beam 2 of X-rays or of gamma rays through a first collimator 3 comprising a plurality of slots defining a very narrow incident beam 4 which is constituted by a plurality of elementary beams, which beams penetrate through a front face that serves as a reference plane 5, into adjacent media to be analyzed 6a, 6b, and 6c and given an overall reference 6, which media are of different densities and are separated from one another by respective separation planes 7.

In this example, the front face of that one of the media which is used as the reference plane 5 is assumed to be plane and parallel to the plane 7. If the assumption is not true, it is possible to use any other surface or plane that is capable of serving as a fixed reference for measurements of distances from the separation plane.

The beam 8 of radiation diffused by the Compton effect reaches a second collimator 9 that includes a plurality of slots defining an acceptance solid angle for a detected beam 10 as received by a receiver R, given reference 11 and situated behind the second collimator 9. The two beams 4 and 10 are pointed in such a manner as to cause them to intersect and define an elementary volume 12 that may be occupied by one of said media 6 and from which Compton effect emission is received by the receiver 11.

To facilitate mechanical adjustments and to ensure stability, the emitter 1, the receiver 11, and the two collimators 3 and 9 are fixed on a common rigid support 13, thereby constituting a measurement assembly 14. The measurement assembly 14 is then displaced relative to the media 6 to be analyzed, or conversely the media 6 are displaced relative to the assembly, so as to enable various different depths and various different locations beneath the front face 5 to be scanned.

A computer 20 includes a time base 21 governing the sequencing of successive measurement cycles, each relating to a given position of said elementary volume 12 within the media 6. The time base controls displacement apparatus 22 for achieving relative displacement between the measurement assembly 14 and the media 6 by means of stepper motors 23 serving at least to vary the distance between the measurement assembly 14 and the reference plane 5 through a certain number of unit steps relative to an initial position, thereby performing one of said sequences of measurement cycles, and serving optionally to displace the measurement assembly 14 in one or two directions (not shown) parallel to said reference plane 5 so as to perform other sequences of measurement cycles relating to elementary volumes lying on other perpendiculars to the reference plane 5.

The output from the receiver 11 is connected to an integrator 24 that may be situated within the computer 20 or else in the vicinity of the receiver 11 so as to avoid receiving electrical noise, the integrator receiving a first signal representative of the number of photons received by the receiver 11, which signal is transmitted from the receiver to the integrator 24 that is under the control of said time base 21. The integrator 24 delivers a second signal representative of the time integral of said first signal to a subtractor 25 in the computer 20 and under the control of the time base 21. This second signal is also applied to a first terminal B1 that enables a user to obtain said second signal directly, which signal varies with the density of the medium 6 occupied by the elementary volume 12 under analysis. The subtractor 25 stores said second signal, and on the basis thereof, it provides a third signal representative of the difference between the second signal that has just been received and the second signal received during the preceding cycle. This third signal is applied to first calculation means 26 under the control of the time base 21 and serving to provide a fourth signal representative of the derivative of said third signal relative to the distance of said reference plane 5 by dividing said third signal by the number of elementary steps through which the measurement assembly 14 was moved at the beginning of the current cycle. Clearly, such a division operation is required only if the measurement assembly 14 is capable of being displaced through different number of steps in different cycles.

The said fourth signal is transmitted to a second calculation means 27 of said computer 20 under the control of the time base and providing a fifth signal and having the same sign as the fourth signal and whose absolute value is equal either:

to the difference obtained by subtracting a predetermined positive number from said fourth signal, so long as the result of said subtraction is positive; or else to zero when the above result is negative or zero.

The fifth signal is applied to third calculation means 28 of said computer 20 under the control of the time base 21 and via a first input, with the third calculation means having second and third inputs via which it receives the control signals issued to the displacement apparatus by the time base 21 respectively for displacement in a direction perpendicular to the reference plane 5 and for displacement in one (or two) direction(s) parallel to said plane 5. This third calculation means 28 stores the fifth signal and, when said fifth signal is zero or of opposite sign to the fifth signal generated during the preceding cycle, it provides a sixth signal on a terminal B2 and representative of a displacement distance of the measurement assembly 14 from its initial position at the beginning of the sequence of cycles, which distance corresponds to the relative position of the barycentre of the successive distances relating to the most recent sequence of successive non-zero and same-sign fifth signals calculated during the preceding cycles, with each such fifth signal being used to weight the displacement distance of the measurement assembly 14 from its initial position during the cycle in which the said fifth signal was recorded.

Since said barycentre is representative of the position of the plane 7 between two media of different densities, the sixth signal is thus correspondingly representative of the position of the separation plane 7 between adjacent media of different densities.

In order to obtain good accuracy in determining the number of photons emitted by the Compton effect, various means are implemented.

Firstly, the source of X-rays or of gamma rays is a stable source delivering radiation of regulated intensity, thereby enabling results obtained at different instants to be compared validly.

Figure 2:
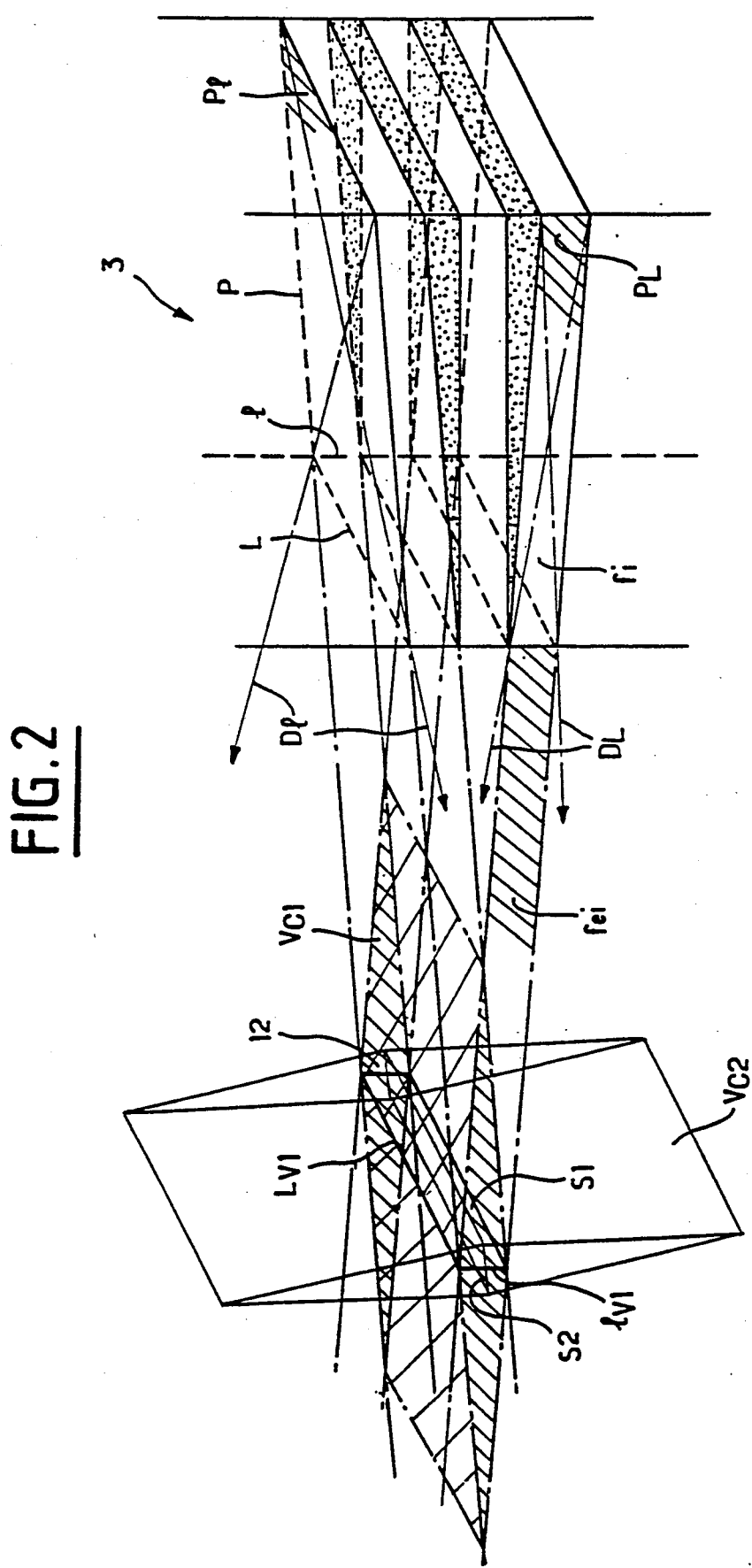
FIG. 2 shows a collimator including a plurality of slots in accordance with the invention.

Secondly, the divergence of the beam 2 leaving the emitter 1 is reduced by passing through the collimator 3 that includes a plurality of slots fi (where i is a positive integer), as shown in FIG. 2. Each of the slots has a depth P of about 200 mm in the propagation direction of the beam, and a section of length L equal to about 6 mm and of width l lying in the range 0.1 mm to 0.4 mm.

Each slot fi is delimited by metal walls which stop the radiation, with the wall Pl perpendicular to the width direction l being very thin. In order to clarify the drawing, the relative sizes of l, L, and P are distorted. The divergence of the elementary beam fei (where i is a positive integer) from each slot fi in the plane PL perpendicular to the length L is very small because of the very small ratio between the width l and the depth P of each slot fi. Each of the two extreme rays is marked by a line whose axis is referenced DL. In contrast, in the plane Pl perpendicular to the width l of the slot fi, the divergence is considerably greater because the ratio of the length L relative to the depth P is greater than the ratio of the width l to the depth. Each of the two extreme rays is referenced by a line of axis Dl. As a result, each elementary beam fei has a section of very narrow width, of the same order of magnitude as the width l of the slot fi, whereas the length of its section is much larger, being of the order of the length L of the slot fi.

The loss of radiation intensity corresponding to the difference between the incident beam 2 on the first collimator 3 and the beam 4 leaving the collimator, is thus due above all to the rays that are absorbed by the larger two parallel walls Pl that are perpendicular to the width direction l of the slot fi.

To obtain a greater total intensity within the irradiated medium 6, the number of such slots is increased by stacking them in the width direction l, so as to obtain about thirty slots (i=1 to 30), of which only three are shown, thus making it possible (ignoring losses) to pick up a large portion of the flux leaving the outlet aperture of the emitter 1, and thereby defining about thirty elementary beams fei that are quasi-parallel and adjacent in quasi-parallel planes Pl.

Each of these slots fi points in such a direction that the set of elementary beams fei passing through respective ones of said slots fi converge on a common surface S1 which is parallel to the face of said collimator 3 from which the beams 4 leave. The width lv of the surface S1 is close in size to the width l of the slots fi, and its length Lv is close in value to the length L. The set of elementary beams fei passes through a first common volume Vc1 that contains said surface S1.

The volume Vc1 may be elongate in shape, of length determined by the length L of the slots.

In similar manner, the second collimator 9 is made identically to the first collimator 3 and the set 10 of elementary beams fei that it receives as transmitted via each of its slots fi defines a second volume Vc2 that includes a surface S2 corresponding to S1 and intersecting it or being close thereto. The two volumes Vc1 and Vc2 define a common volume which is the above-mentioned elementary volume 12 of small size, of approximately lozenge-shaped section, and of length extending over the length of the incident beam 4 or of the received beam 10, as determined by the length L of the slots fi. At the inlet to the receiver 11, a detector of area substantially equal to the section of the received beam 10 transforms the received photons into an electrical signal which constitutes said first signal representative of the number of received photons.

The first and second collimators 3 and 9 are placed in such a manner that the outlet section of each slot fi has its length L extending parallel to the reference plane 5. As a result, all of the points of said elementary volume 12 are situated at substantially equal distance from said reference plane 5 which coincides with the front face of one of the media 6 and which is assumed to be parallel to the looked-for planes 7 between the media of different densities. As a result, all of the points in said elementary volume 12 situated at the same distance from the reference plane 5 are in material of the same density, and therefore they emit identical signals that may be added together.

The system operates as follows. The measurement assembly 14 is placed in an initial position situated at a determined distance from the media 6 to be analyzed so that said elementary volume 12 can be displaced and so that it intersects the plane 7 separating said media 6 substantially perpendicularly to the reference plane 5.

The computer 20 then uses the time base 21 to organize a sequence of measurement and calculation cycles, with each such cycle being related to a determined relative displacement of the measurement assembly 14 relative to the reference plane 5 and relative to an initial position defined in this way, with relative displacement taking place in a direction substantially perpendicular to said reference plane 5 and thus to the plane 7 separating the media 6. One such cycle is described below.

Initially the time base 21 issues a first relative displacement command (advance in the example describe) to cause the measurement assembly 14 to move relative to the media 6 by sending an advance instruction to the stepper motor 23 that controls displacement in the direction perpendicular to the reference plane 5.

Thereafter, the time base 21 instructs the integrator 24 to begin integrating by applying a second command thereto that constitutes a beginning-of-integration instruction. The first signal from the receiver 11 is then integrated relative to time. A third command causes integration to cease and is transmitted by the time base 21 to said integrator 24 after a predetermined time lapse, thereby stopping integration. The resulting integrated signal constitutes the second signal and is received by the subtractor 25.

The time base 21 then issues a third command which is received by the subtractor 25 which then begins by storing said third signal in read/write memory. The subtractor then reads from the memory the value of the third signal which it has just received together with the value of the third signal that it received during the preceding cycle, with the preceding value being subtracted from the third signal that has just been received (e.g. digitally) and with the result constituting a fourth signal representative of the derivative of said third signal relative to the length of the displacement performed at the beginning of the current cycle. If the length of this displacement may vary from one cycle to another, said third signal is then divided by the length of said displacement at the beginning of the current cycle, thereby providing said fourth signal representative of the derivative of said third signal relative to the measured length in the displacement direction.

The time base 21 then issues a fourth command which is received by the second calculation means 27 which receives the fourth signal and which supplies a fifth signal, as explained above, corresponding to the amount by which the fourth signal exceeds said positive predetermined number constituting a threshold.

The time base 21 then applies a fifth command to the third calculation means 28 which then stores said fifth signal and optionally calculates the barycentre (as explained above), in which case it provides said sixth signal on the terminal B2, which signal is representative of the relative position of a plane 7 separating two media of different densities and expressed in the form of the value of the relative displacement of the measurement assembly 14 relative to the media 6 in the direction perpendicular to the plane 7 separating the media.

In order to obtain an absolute position reference, the third calculation means 28 may translate the displacement of the measurement assembly 14 relative to its initial position into a displacement relative to the reference plane 5, which is taken, for example, as being the front face of the medium 6, providing it is plane and parallel to the separation planes 7.

The initial position of the elementary volume 12 may also be used as a reference, with its distance from the measurement assembly 14 being fixed and known by triangulation of the two beams 4 and 8.

Another method consists in causing the elementary volume 12 to pass through the front face of the medium 6, thereby obtaining accuracy equal to the subsequent determinations of the positions of the separation planes 7 and thus avoiding errors in the measurement of the distance between the measurement assembly 14 and the reference plane 5 constituted by the front face of one of the media 6.

The sequence of positions determined for the various separation planes 7 between the media can be used to deduce the thickness of each of the media and the accurate position thereof by calculating the differences between the positions of said separation planes 7.

We claim:

1. A system for locating the separation plane between two media of different densities, relative to a reference plane parallel to said separation plane and at a fixed distance therefrom, said media being suitable for being irradiated by a beam of X-rays or of gamma rays from an emitter, and producing scattering by the Compton effect, which scattering is detected by a receiver that responds thereto by providing a first signal, said receiver being carried by a support; wherein:
    said emitter emits at regulated intensity; and
    said system further includes:
    a time base emitting sequencing commands for cycles in a sequence of displacement, measurement, and calculation operations, with one such sequence of cycles corresponding to measurements relating to a sequence of analyzed volumes disposed along a line substantially perpendicular to said reference plane;
    displacement apparatus for controlled relative displacement of said support relative to said reference plane and substantially perpendicular thereto, said apparatus being controlled by the time base;
    a first collimator including at least one slot, said collimator being fixed on said support and providing an elementary beam passing through said slot and directed towards an elementary volume of elongate shape extending parallel to the looked-for separation plane between the media, which elementary volume is capable of being occupied by said media, which collimator being situated at the outlet from the emitter;
    a second collimator including a plurality of slots, said second collimator being fixed on said support, its slots converging on said elementary volume such that the elementary beams passing through the slots are concentrated in said elementary volume, which second collimator is situated in front of the detector of the receiver;
    said support, said emitter, said first and second collimators, and said receiver constituting a measurement assembly whose position relative to said reference plane is identical to that of said support;
    an integrator for integrating relative to time and under the control of said time base, said integrator receiving said first signal and providing a second signal representative of the time integral of said first signal over a time period defined by the time base;
    a subtractor controlled by said time base, receiving said second signal and responding thereto by providing a third signal representative of the difference between said second signal relating to the current cycle and the second signal relating to the preceding cycle;
    first calculation means controlled by said time base, receiving said third signal and responding thereto by providing a fourth signal representative of the derivative of said third signal relative to the relative displacement distance between the measurement assembly and the reference plane;
    second calculation means controlled by said time base, receiving said fourth signal and responding thereto by providing a fifth signal representative of a number having the same sign as the fourth signal and whose absolute value is equal either:
        to the difference obtained by subtracting a predetermined positive number from said fourth signal, so long as the result is positive; or else
        to zero whenever said result is negative or zero;
    third calculation means controlled by said time base, having a first input receiving said fifth signal and having a second input receiving the command issued by the time base for causing relative displacement of said support relative to the reference plane in a direction substantially perpendicular thereto, said third calculation means storing said fifth signal and, whenever said fifth signal is zero or opposite in sign to the fifth signal generated during the preceding cycle, providing a sixth signal representative of a displacement distance of the measurement assembly relative to its initial position at the beginning of said sequence of cycles, which distance corresponds to the relative position of the barycentre of successive distances relating to the most recent sequence of non-zero and same-sign fifth signals calculated during the preceding cycles, with the value of each such fifth signal of such a sequence weighting the displacement distance at which the measurement assembly is to be found from its initial position during the cycle in which said fifth signal is generated, said barycentre being situated in a separation plane between two adjacent media.

2. A system according to claim 1, wherein said first collimator includes a plurality of slots, and in which the elementary beams passing through said slots converge on said elementary volume.

3. A system according to claim 1, including apparatus for displacing the measurement assembly relative to the media in a direction parallel to said reference plane.

4. A system according to claim 1, wherein all of the elementary beams, each transmitted via one of the slots, are concentrated in the same common volume, one of whose dimensions lies in the range 0.1 mm to 0.4 mm.

5. A method of localizing the separation plane between two media of different densities, relative to a reference plane parallel to said separation plane and at a fixed distance therefrom, said media being suitable for being irradiated by a beam of X-rays or of gamma rays from an emitter and producing Compton effect scattering that is detected by a receiver which responds thereto by providing a first signal, said receiver being carried by a support, wherein the method comprises a sequence of cycles corresponding to measurements relating to a sequence of analyzed volumes spaced apart along a line substantially perpendicular to said reference plane, each of said cycles including the following steps:

controlling a displacement apparatus to obtain controlled displacement of said support relative to said reference plane in a direction substantially perpendicular thereto;

emitting a beam of X-rays or of gamma rays at regulated intensity from an emitter fixed on said support;

spatially filtering said beam by passing it through a first collimator that includes at least one slot, the collimator being fixed on said support and the elementary beam passing through said slot being directed towards an elementary volume of elongate shape extending parallel to the looked-for separation plane between the media, which elementary volume is capable of being occupied by said media, said first collimator being situated at the outlet from the emitter;

spatially filtering the Compton effect radiation emitted by said elementary volume by passing the radiation through a second collimator that includes a plurality of slots, the second collimator being fixed on said support, the slots converging on said elementary volume such that the elementary beams passing through the slots are concentrated in said elementary volume, the collimator being situated in front of the detector of the receiver, said support, said emitter, said first and second collimators and said receiver constituting a measurement assembly whose position relative to the said reference plane is identical to that of said support;

integrating said first signal relative to time in an integrator for performing integration relative to time under the control of the time base, which integrator receives said first signal and provides a second signal representative of the time integral of said first signal over a time period defined by the time base;

subtracting the second signal relating to the preceding cycle from said second signal relating to the current cycle in a subtractor controlled by said time base and receiving said second signal, thereby obtaining a third signal;

differentiating said third signal relative to the relative displacement distance between the measurement assembly and the reference plane in a first calculation means controlled by said time base and receiving said third signal, thereby obtaining a fourth signal;

calculating a number in a second calculation means controlled by said time base and receiving said fourth signal the sign of said number being identical to that of the fourth signal, and its absolute value being equal either to the difference obtained by subtracting a predetermined positive number from said fourth signal, when the result of the subtraction is positive, or else is equal to zero when said result is negative or zero, thereby obtaining a fifth signal;

calculating a sixth signal in a third calculation means controlled by said time base and having a first input receiving said fifth signal and a second input receiving the command issued by the time base to cause relative displacement of said support relative to the reference plane and substantially perpendicular thereto, the third calculation means storing said fifth signal and generating said sixth signal when said fifth signal is zero or of opposite sign to the fifth signal generated during the preceding cycle, said sixth signal being representative of a displacement distance of the measurement assembly relative to its initial position at the beginning of said sequence of cycles, which distance corresponds to the relative position of the barycentre of successive distances relating to the most recent sequence of non-zero fifth signals of the same sign calculated during the preceding cycles, the value of each such fifth signal of such a sequence weighting the displacement distance at which the measurement assembly is to be found from its initial position during the cycle in which said fifth signal is generated, said barycentre being situated in a separation plane between two adjacent media.

6. A method according to claim 5, wherein a first collimator is usued that is provided with a plurality of slots passed through by a plurality of elementary beams converging on said elementary volume.

* * * * *